United States Patent [19]

Keyomarsi et al.

[11] Patent Number: 5,543,291
[45] Date of Patent: Aug. 6, 1996

[54] METHOD OF DETECTING CARCINOMA

[75] Inventors: Khandan Keyomarsi; Arthur B. Pardee, both of Brookline, Mass.

[73] Assignee: Dana Farber Cancer Institute, Boston, Mass.

[21] Appl. No.: 11,187

[22] Filed: Jan. 29, 1993

[51] Int. Cl.$^6$ .................. G01N 33/574; C12Q 1/68
[52] U.S. Cl. .................. 435/6; 435/7.23; 436/63; 436/64; 436/813
[58] Field of Search .................. 435/7.23, 6; 436/63, 436/64, 813

[56] References Cited

U.S. PATENT DOCUMENTS

| | | | |
|---|---|---|---|
| 4,968,603 | 11/1990 | Slamon et al. | 435/6 |
| 5,085,983 | 2/1992 | Scanlon | 435/6 |

FOREIGN PATENT DOCUMENTS

| | | |
|---|---|---|
| 0390323 | 2/1990 | European Pat. Off. |
| WO92/15603 | 9/1992 | WIPO |
| WO92/20796 | 11/1992 | WIPO |
| WO92/19258 | 11/1992 | WIPO |
| WO93/06123 | 4/1993 | WIPO |

OTHER PUBLICATIONS

Keyomarsi, K., et al., *Proc. Annu. Meet. Am. Assoc. Cancer Res.*, 37:A246, 1993.

Shrestha, P., et al., *Virchows Arch. A. Pathol. Anat. Histopathol.*, 421(3), pp. 193–202, 1992.

Bravo, R. et al., "Identification of a nuclear polypeptide (cyclin) whose relative proportion is sensitive to changes in the rate of cell proliferation and to transformation", Prog. Clin. Biol. Res. 85:235–248 (1982).

Runnebaum, I. B., et al., "Mutations in p53 as potential molecular markers for human breast cancer", Proc. Natl. Acad. Sci. USA 88:10657–10661 (1991).

Hunter, T., et al., "Cyclins and Cancer", Cell 66:1071–1074 (1991).

Kurki, P., et al., "Expression of Proliferating Cell Nuclear Antigen (PCNA)/Cyclin during the Cell Cycle", Exp. Cell Res. 166:209–219 (1986).

Celis, J. E., et al., "Nuclear Patterns of Cyclin (PCNA) Antigen Distribution Subdivide S–Phase in Cultured Cells—Some Applications of PCNA Antibodies", Leukemia Res., 10(3):237–249 (1986).

Celis, J. E., et al., "Cyclin: A Nuclear Protein Whose Level Correlates Directly with the Proliferative State of Normal As Well as Transformed Cells", Leukemia Res. 8(2):143–157 (1984).

Liu, Y.-C., et al., "Gene Expression of PCNA/Cyclin in Adult Tissues and the R3230AC Mammary Tumor of Rat", Biochem. & Biophys. Res. Comm. 161(2):873–882 (1989).

Luqmani, Y. A., et al., "Polymerase Chain Reaction–Aided Analysis of Gene Expression in Frozen Tissue Sections", Analytical Biochem. 200:291–295 (1992).

Liang, P., et al., "Differential Display and Cloning of Messenger RNAs from Human Breast Cancer versus Mammary Epithelial Cells", Cancer Res. 52:6966–6968 (1992).

Lees, E, et al., "Cyclin E/cdk2 and cyclin A/cdk2 kinases associate with p107 and E2F in a temporally distinct manner", Genes & Develop. 6:1874–1885 (1992).

Koff, A., et al., "Human Cyclin E, a New Cyclin That Interacts with Two Members of teh CDC2 Gene Family", Cell, 66:1217–1228, (1991).

Dulic, V., et al., "Association of Human Cyclin E with a Periodic $G_1$–S Phase Protein Kinase", Science 257:1958–1961 (1992).

Koff, A., et al., "Formation and Activation of a Cyclin E–cdk2 Complex During the $G_1$ Phase of the Human Cell Cycle", Science, 257:1689–1694 (1992).

Ohtsubo, M., et al., "Cyclin–Dependent Regulation of $G_1$ in Mammalian Fibroblasts", Science, 259:1908–1912 (1993).

Lew, D. J., et al., "Isolation of Three Novel Human Cyclins by Rescue of G1 Cyclin (Cln) Function in Yeast", Cell, 66:1197–1206 (1991).

Schuuring, Els Verhoeven, et al., "Identification and cloning of two overexpressed genes, U21B31/PRAD1 and EMS1, within the amplified chromosome 11q13 region in human carcinomas", Oncogene, 7(2):355–361 (1992).

Keyomarsi, Khandan et al., "Redundant cyclin overexpression and gene amplification in breast cancer cells", Proc. Natl. Acad. Sci. USA, 90(3):1112–1116 (1993).

Keyomarsi, Khandan, et al., "Cyclin E, a Potential Prognostic Marker for Breast Cancer", *Cancer Research* 54:380–385 (1994).

Buckley, Michael F., et al., "Expression and amplification of cyclin genes in human breast cancer", *Oncogene*, 8(8):2127–2133 (1993).

Lut, X. P., et al., "Induction of Cyclin mRNA and Cyclin-associated Histone H1 Kinase during Liver Regeneration", *The Journal of Biological Chemistry*, 267(5):2841–2844 (1992).

*Primary Examiner*—Toni R. Scheiner
*Attorney, Agent, or Firm*—Hamilton, Brook, Smith & Renolds, P.C.

[57] ABSTRACT

A method of detecting carcinoma, particularly breast carcinoma, in a test sample of tissue, comprising assessing the expression cyclin E, or the amplification of cyclin genes, particularly the cyclin E gene, is disclosed. Altered expression of cyclins, such as overproduction of cyclins, particularly cyclin E, or production of alternative cyclin E proteins, as well as deranged appearance of mitotic cyclins during the cell cycle, are indicative of the presence of carcinoma. Amplification of cyclin genes, particularly the cyclin E gene, is also indicative of the presence of carcinoma.

39 Claims, 1 Drawing Sheet

METHOD OF DETECTING CARCINOMA

FUNDING

Work described herein was supported in part by National Institutes of Health grants CA 22427, S07RR05526-29, as well as National Research Service Award CA08949-01 from the National Institutes of Health. The United States Government has certain rights in the invention.

BACKGROUND OF THE INVENTION

Cyclins were first identified in marine invertebrates on the basis of their dramatic cell cycle periodicity during meiotic and early mitotic divisions (Evans et al., *Cell* 33:389–396 (1983); Swenson et al., *Cell* 47:861–870 (1986); Standart et al., *Dev. Biol.* 124:248–254 (1987)). Over 30 cyclin sequences are now available for comparison. They fall into three categories; A-type, B-type, and Gl-cyclins (C, D1-D3, and E). These can be distinguished on the basis of conserved sequence motifs, patterns of appearance, and apparent functional roles during specific phases and checkpoints of the cell cycle in a variety of species (Hunt, T., *Nature* 350:462–463 (1991); Xiong, Y. and Beach, D., *Curr. Biol.* 1:362–364 (1991)).

Cyclins function by forming a complex with and activating a family of cyclin-dependent protein kinases (CDKs), at various stages in the cell cycle. The activated kinase starts a complex kinase cascade that directs the cell into DNA synthesis and/or mitosis (Draetta, G., *Trends Biochem.* 15:378–383 (1990); Tsai et al., *Nature* 353:174–177 (1991); Pagano et al., *EMBO J* 11:961–971 (1989)). Since the major regulatory events leading to proliferation in animal cells occur in the G1 phase of the cell cycle (Pardee, A.B., *Science* 246:603–608 (1989)), the deranged expression of cyclins and CDKs active in G1 may be the key to oncogenesis.

The link between oncogenesis and cyclins has been made with discovery of inappropriate expression of two cyclins in tumors (Hunter, T. and Pines, J., *Cell* 66:1071–1074 (1991)). First, the cyclin A gene is the site of integration of a fragment of hepatitis B virus genome in a hepatocellular carcinoma (Wang et al., *Nature* 343:555–557 (1990)). Cyclin A is also associated with the adenovirus transforming protein E1A in adenovirus-transformed cells (Pines, J. and Hunter T., *Nature* 346:760–763 (1990)). Second, in some parathyroid tumors, the Pradl (cyclin D1) locus is overexpressed due to a chromosomal rearrangement translocating it to the enhancer of the parathyroid hormone gene (Motokura et al., *Nature* 350:512–515 (1991)). Recently, translocation/amplification of cyclin D1 has been associated with a small percentage of other cancers including, centrocytic lymphomas, squamous cell, esophageal, and breast carcinomas (Schuuring et al., *Oncogene* 7:355–361 (1992); Laramie et al., *Oncogene* 6:439–444 (1991); Jiang et al., *Cancer Res.* 52:2980–2983 (1992)).

Although these observations emphasize the importance of cyclins in cancer, the question remains of how the altered expression of only two different cyclins (i.e., cyclins A and D1), which are only very occasionally deranged, can be responsible for transformation. As yet, there have been no clear connections between cyclin derangements and cancer involving the aberrant expression of more than one cyclin, or any of the CDKs, in one type of cancer. A survey of all cyclins and CDKs in the same system of normal vs. tumor cells is essential to show whether cyclins can function collectively or redundantly in cancer by bypassing crucial checkpoints in the cell cycle.

SUMMARY OF THE INVENTION

The invention pertains to a method of diagnosing the presence of human carcinoma, particularly human breast carcinoma, by examining a sample of tissue for the presence of aberrant expression of cyclin E. As described herein, Applicants have demonstrated the presence of abnormal expression of various cyclins and CDKs in human breast cancer cell lines, compared to expression in normal mammary epithelial cells. In particular, altered expression of cyclin E protein was found in all tumor lines studied. Altered expression included: gens amplification, overexpression of cyclin E or both; and expression in tumor lines of one, two or three sizes (50, 42 and 35 kDa) of cyclin E related protein, in contrast to expression of one major protein of approximately 50 kDa, as demonstrated by use of a cyclin E antibody specific for cyclin E protein. A deranged order of appearance of cyclins during the cell cycle, particularly the untimely appearances of mitotic cyclins prior to G1 cyclins in synchronized tumor vs. normal cells, has also been shown. In addition, increased cyclin mRNA stability in tumor lines, as well as general overexpression of other cyclins, has also been shown by Applicants.

As a result of these findings, Applicants have designed a diagnostic test for human carcinomas, such as human breast carcinoma, in which the expression of cyclin E protein is deranged, the order of appearance of cyclins is deranged, or both are deranged. In the method, a test tissue sample from an individual suspected of having cancer, such as breast tissue from an individual, is obtained, and protein expression, particularly cyclin E expression, is assessed using known methods, such as Western blotting. The results from the test sample are compared to the results from a control sample of normal tissue, such as normal breast tissue, from the same individual or from another individual, to determine whether cyclin E expression in the sample tissue is aberrant or deranged. Aberrant expression of cyclin E in the test tissue sample is indicative of the presence of carcinoma cells.

BRIEF DESCRIPTION OF THE FIGURES

FIGS. 1, 2: cyclin E expression shown by a monoclonal antibody to cyclin E; FIGS. 3, 4: expression shown by a polyclonal antibody. FIGS. 1, 3: normal adjacent tissue; FIGS. 2, 4: cancer tissue. Lanes in all figures were as follows: (1) metastatic ductal carcinoma; (2) invasive, poorly differentiated ductal carcinoma of the breast; (3) infiltrating ductal carcinoma; (4) metastatic ductal carcinoma; (5) inflammatory breast cancer; (6) malignant phylloides tumor; (7) infiltrating and in-situ ductal carcinoma; (8) small foci of in-situ ductal carcinoma; and (9) infiltrating ductal carcinoma.

DETAILED DESCRIPTION OF THE INVENTION

Figure 1:
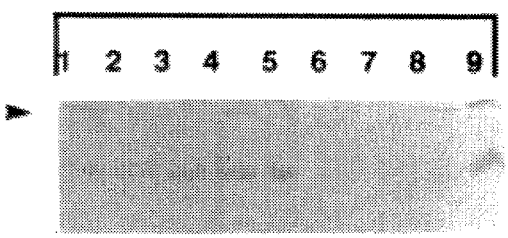
FIGS. 1, 2, 3 and 4 comprise a series of Western blots depicting the aberrant expression of cyclin E protein in breast cancer vs. normal adjacent tissues.

The invention described herein is based on Applicants' discovery that cyclin expression in human breast tumor cells, in comparison to normal human breast cells, is altered in several ways. As described below, Applicants have discovered that: (1) deranged expression of cyclin E protein, including overexpression of cyclin E or overexpression of cyclin E related proteins not seen in normal cells, occurred in 10 of 10 tumor lines; (2) increased mRNA stability of all cyclins and CDKs, was evident in one tumor line, (3)

untimely appearance of the mitotic cyclins occurred at the G1 phase of the tumor cell cycle; (4) general overexpression of mRNAs and proteins for cyclins A and B and CDC2 occurred in 9 of 10 tumor lines and 3 of 3 tumor tissue samples; and (5) amplification of the cyclin E gene occurred in 1 of 10 cell lines. The aberrant expression of cyclin E was particularly noteworthy: in normal breast tissue cells, cyclin E antibody recognized a single cyclin E protein of approximately 50 kDa; in cancerous breast tissue cell lines, however, cyclin E antibody recognized three proteins, of approximate size 50, 42, and 35 kDa. All tumor lines overexpressed one, two, or all three of these proteins, referred to herein collectively as cyclin E proteins because they are all recognized by antibody known to be specific for cyclin E. The 42 and 35 kDa proteins are also referred to as cyclin E related proteins.

As a result of the work described herein, a method of diagnosing the presence of human carcinoma, particularly breast carcinoma, is now available. The method is exemplified by detection of breast carcinoma, but can be applied to assessment of other types of carcinomas in which it is shown that cyclin expression is characteristically altered or deranged in such a manner that tumor cells can be distinguished or differentiated from normal (non-cancerous) cells on the basis of differential or altered cyclin expression. In the method, a test sample of tissue thought to be cancerous is obtained from an individual. The test sample of tissue is obtained by surgical methods, such as excision of the tumor. Alternatively, the test sample can be a blood sample from the individual suspected of having cancer; this sample is obtained by known methods. Expression or presence of cyclins in the test sample is assessed by identifying cyclin expression product(s) using anti-cyclin agent(s) which is detectably labelled, or which can be subsequently detectably labelled; in particular, antibodies which recognize the known cyclin proteins can be used. The extent to which the known cyclin proteins are expressed or are present in the test sample is then determined by any means, such as by western blot. For example, a cell lysate preparation can be generated from the test tissue sample, and then subjected to western blotting with an anti-cyclin agent such as an antibody or antibodies which recognize the 50 kDa, 42 kDa, and 35 kDa cyclin E proteins. The extent to which the cyclin E proteins are expressed in the test tissue sample is assessed.

Cyclin expression or presence in the test sample is compared with the results from a comparable control sample of normal tissue or blood, in which cyclin expression or presence is determined and quantitated with the same approach as used for the test sample. The control sample can be normal tissue from the same individual or from another individual. For example, in examination of a suspected breast cancer, the control sample used for comparison can be a sample of normal mammary cells from the individual suspected of having breast carcinoma. These normal cells can be collected from a site adjacent to the tissue suspected of containing carcinoma cells, such as normal tissue adjacent to the biopsy site. Alternatively, the control sample can be a sample of comparable normal cells obtained from another individual, such as normal mammary epithelial cells from a reduction mammoplasty, or a blood sample from another individual. The control sample can be obtained at the same time as the test sample, or can be a pre-established control for which the cyclin expression was determined at an earlier time.

Aberrations in cyclin expression, particularly cyclin E expression, in the test sample as compared with expression in the control sample, are indicative of cancer. As used herein, the term "abnormal," "aberrant," or "deranged" expression refers to expression of cyclin E (50 kDa, 42 kDa and/or 35 kDa size) that differs in kind or in quantity from cyclin E expression in normal tissue. For example, overexpression of any one or more of the cyclin E proteins (50 kDa, 42 kDa, and/or 35 kDa protein recognized by a cyclin E specific recognition agent, such as an antibody which recognizes cyclin E) in the test sample is indicative of cancer. Deranged order of expression of cyclins during the cell cycle is also indicative of cancer: for example, expression of mitotic cyclins before the $G_1$ cyclins is indicative of cancer. In particular, appearance of cyclins B and A before cyclins D1, D3, C or E is indicative of carcinoma in breast tissue samples.

The agent used in the present invention method to determine cyclin expression in tissue samples will generally be an antibody. However, it can be another agent, such as a cDNA, which recognizes and binds the cyclin to be assessed in the sample and allows its presence in the sample to be detected and/or quantitated. The antibody or other agent used will recognize cyclin E or another cyclin (A, B, C, D1, D3) or their dependent kinases (e.g., CDC2 for mitotic cyclins and CDK2 for the G-1 cyclins) and can be used individually or as a set or panel.

The term antibody, as used herein, is intended to encompass both polyclonal and monoclonal antibodies. The term antibody is also intended to encompass mixtures of more than one antibody reactive with cyclin E (e.g., a cocktail of different types of monoclonal antibodies reactive with cyclin E). The term antibody is further intended to encompass whole antibodies, biologically functional fragments thereof, and chimeric antibodies comprising portions from more than one species, bifunctional antibodies, etc. Biologically functional antibody fragments which can be used are those fragments sufficient for binding of the antibody fragment to cyclin E.

The chimeric antibodies can comprise portions derived from two different species (e.g., human constant region and murine variable or binding region). The portions derived from two different species can be joined together chemically by conventional techniques or can be prepared as single contiguous proteins using genetic engineering techniques. DNA encoding the proteins of both the light chain and heavy chain portions of the chimeric antibody can be expressed as contiguous proteins.

Monoclonal antibodies reactive with cyclin E can be produced using somatic cell hybridization techniques (Kohler and Milsrein, *Nature* 256:495–497 (1975)) or other techniques. In a typical hybridization procedure, a crude or purified protein or peptide comprising at least a portion of cyclin E can be used as the immunogen. An animal is vaccinated with the immunogen to obtain anti-cyclin E antibody-producing spleen cells. The species of animal immunized will vary depending on the species of monoclonal antibody desired. The antibody producing cell is fused with an immortalizing cell (e.g., myeloma cell) to create a hybridoma capable of secreting anti-cyclin E antibodies. The unfused residual antibody-producing cells and immortalizing cells are eliminated. Hybridomas producing desired antibodies are selected using conventional techniques and the selected hybridomas are cloned and cultured.

Polyclonal antibodies can be prepared by immunizing an animal with a crude or purified protein or peptide comprising at least a portion of cyclin E. The animal is maintained under conditions whereby antibodies reactive with cyclin E are produced. Blood is collected from the animal upon reaching a desired titer of antibodies. The serum containing the polyclonal antibodies (antisera) is separated from the other blood components. The polyclonal antibody-containing serum can optionally be further separated into fractions of particular types of antibodies (e.g., IgG, IgM).

In another embodiment of the current invention, the test sample can be examined for amplification of a cyclin gens. Amplification of the cyclin gene in the tissue sample is assessed by identifying the copy number of the cyclin gens using an agent(s) which is detectably labelled, or which can be subsequently detectably labelled. The copy number is then determined by any means, such as by Southern blot. For example, a test tissue sample from an individual suspected of having breast cancer can be examined, through Southern blot analysis of the DNA in the cells of the sample, for amplification of the cyclin E gene. Amplification of the cyclin E gene in the cells of the test sample, as compared with cells of a control sample, is indicative of carcinoma. As used herein, "amplification" of a cyclin gene includes amplification of all or a portion of the gene.

The methods described herein can be used to detect any type of cancerous cells or conditions for which aberrant or deranged cyclin expression, or amplification of a cyclin gene, is a characteristic which distinguishes affected or abnormal tissue or cells (e.g., cancerous or precancerous cells) from normal tissue or cells. Methods used herein to analyze cyclin expression and cyclin gene amplification in breast cell lines and in breast tissue samples, as described below, can be used to analyze cyclin expression and gene amplification in any cell type and, thus, to establish the aberrational or deranged cyclin expression (level of expression, protein(s) expressed, timing or order of expression or cyclins) or the copy number of the cyclin gene, which distinguishes abnormal or affected cells from normal cells. For example, analysis of protein expression in normal and in tumor cells from the cell type to be studied, such as by western blot, will reveal differences in cyclin protein expression, if such differences exist. After synchrony of cells in a culture of the cells to be studied, analysis of expression patterns of cyclins by known methods, such as by northern blot, will reveal levels of cyclin mRNA expression during the course of the cell cycle, if such differences exist. A comparison of mRNA expression in normal cells and in tumor cells will pinpoint differences in temporal cyclin expression. Once it has been determined that there is a characteristic difference between affected cells and normal cells, standards for cyclin expression in normal cells of the same type can be established and the methods described herein can be used to detect carcinoma in the cell type.

The following is a description of Applicants+ assessment of cyclin expression in breast tissues and in normal and cancerous breast cell lines; amplification of the cyclin E gene in a tumor cell line; cell cycle expression of mRNAs in both normal and tumor cells; the mechanism of mRNA overexpression; and the implications of deranged cyclin expression for oncogenicity.

A. Overexpression of Cyclins in Breast Tissues

In order to examine directly the relevance of cyclin derangement to in vivo conditions, the expression of cyclin mRNAs in breast tumor samples vs. normal adjacent breast tissue was measured. Total RNA was isolated from three human infiltrating ductal and metastatic breast carcinomas and two adjacent nontumorous tissues, and subjected to Northern blot analysis using cyclins A and B and CDC2. These analyses revealed that mRNAs for cyclins A and B as well as CDC2 were significantly overexpressed in tumor samples when compared to the normal adjacent tissue, suggesting that they may be involved in transformation. To determine whether cyclin overexpression is dependent on cell proliferation or represents a true difference between normal and tumor cells, an in vitro system of cultured cells was used.

B. Differential Cyclin Expression in Proliferating Normal vs. Cancerous Breast Cells Ten different breast cancer cell lines were compared against three different proliferating normal mammary epithelial cell strains obtained from reduction mammoplasties and used early, i.e., at passages 9–11 (Band, V. and R. Sager, PNAS USA 86:1249–1253 (1989)) (see Example 3). The tumor cell types, their tumorigenicity potentials, and their estrogen receptor status are listed in Table 1.

TABLE 1

Characterization of normal and tumor-derived breast epithelial cells

| No. | Cell line strain | Cell type | ER status | Tumor-genicity |
|---|---|---|---|---|
| 1 | 70N | N | − | − |
| 2 | 81N | N | − | − |
| 3 | 76N | N | − | − |
| 4 | MCF-7 | A(pc) | + | + |
| 5 | MDA-MB-157 | C(pc) | − | + |
| 6 | MDA-Mb-231 | A(pc) | − | + |
| 7 | MDA-MB-436 | A | − | − |
| 8 | T-47D | DC(pc) | + | + |
| 9 | BT-20 | C | + | + |
| 10 | HBL 100 | T(bm) | − | − |
| 11 | Hs-578T | DC | − | + |
| 12 | SKBR-3 | A(pc) | − | + |
| 13 | ZR75T | IDC | + | + |

N, normal breast cells from reduction mammoplasty; A, adenocarcinoma; pc, pleural effusion; C, carcinoma; DC, ductal carcinoma; T(bm), tumor (breast milk); IDC, infiltrating DC. Estrogen receptor (ER) status of the cell lines were determined by Northern blot analysis using a cDNA to the full-length estrogen receptor as a probe. +, positive; −, negative.

A common pattern of overexpression of the mitotic cyclins A and B and =heir dependent kinase, CDC2, by up to 12 fold, was found in most (9/10) of the tumor cell lines studied. The pattern and extent of overexpression of the cyclin A, cyclin B and p34$^{cdc2}$ proteins were very similar to their mRNAs in most of the tumor lines. These in vitro observations are consistent with the breast tissue results described above, suggesting that cyclin overexpression in tumor cells is not dependent on proliferation, since the normal cell strains used are rapidly proliferating. Hence, the difference in cyclin expression is due to a difference between normal and tumor cells, one that is general among the tumor lines studied.

While the mitotic cyclins and CDC2 are overexpressed in 90% of the tumor lines studied, the G1 cyclins and their dependent kinase, CDK2, are overexpressed in only 50% of the tumor lines. Furthermore, cyclins D1 and D3 (Motokura et al., *J. Biol. Chem.* 267:20412–20415 (1992)) are only moderately overexpressed (Lammie etal., *Oncogene* 6:439–444 (1991)) or even underexpressed in two tumor lines as compared to normal cell strains. Cyclin C mRNA is expressed equally in normal and tumor cells and c-myc mRNA levels in the tumor-lines examined here are generally equal to or lower than normal, as observed [Zajchowski, D. et al., *Cancer Res.* 48: 7041–7047 (1988)].

The most striking abnormality is that of cyclin E expression. A remarkable overexpression of cyclin E mRNA was found in only one tumor line (MDA-MB-157) and moderate overexpression in 5 other tumor lines. Western blot analysis, however, revealed derangements of cyclin E protein in all these tumor lines, including those with no apparent overexpression of cyclin E mRNA. Cyclin E antibody (Dulic et al., *Science* 257:1958–1961 (1992)) recognized one major protein migrating at approximately 50 kDa in the normal mammary epithelial cell lysates, corresponding to the size of the cyclin E protein (Dulic et al., *Science* 257:1958–1961 (1992); Koff et al., *Science* 257:1689–1694 (1992)). In the tumor lines, however, cyclin E antibody recognized three major proteins migrating at 50, 42 and 35 kDa. Each tumor line overexpressed one, two, or all three cyclin E-related proteins, revealing a deranged pattern of cyclin E protein expression that in all cases was different from that of the normal cell strains.

C. Amplification of Cyclin E Gene

Cyclin E overexpression in the MDA-MB-157 cell line at the levels of DNA, RNA and protein was examined, and compared to the expression in normal cell strain 76N. Southern blot analysis revealed S-fold amplification of the cyclin E gene, and no gross genomic rearrangement. No co-amplification of the other cyclin or CDK genes were observed in this tumor line, even though there was a general overexpression (up to 10-fold) of their mRNAs.

Northern blot analysis indicated that although cyclin E mRNA is overexpressed by 64-fold in the tumor cell line, it is present in only one size (2.1 kb) in both the normal and tumor cells. Furthermore, the one size cyclin E mRNA in the tumor line is translated into at least three overexpressed proteins. In the normal cells, cyclin E antibody reacted strongly with only one protein of 50 kDa (Dulic et al., *Science* 257:1958–1961 (1992); Koff et al., *Science* 257:1689–1694 (1992)). The cyclin E proteins in MDA-MB-157 cells have a much higher H1 kinase activity associated with them compared to that of the normal cell strain. Collectively these observations provide the first evidence of a genetic alteration of cyclin E in cancer, implying an oncogenic role.

D. Cell Cycle Expression of Cyclin and CDK mRNAs in Normal vs. tumor cells

To gain insight into the possible functions of cyclins A and B and CDC2, which were overexpressed not only in the three breast tumor tissues examined but also in 90% of all tumor cell lines, the behavior of RNAs in normal and tumor cells was compared through the cell cycle. The normal cell strain examined was 76N; the ZR75T tumor cell line was chosen for this analysis since it is the only one among the 10 studied that overexpressed only cyclins A and B and CDC2 and none of the G1 cyclin mRNAs. ZR75T cells were synchronized in early G1 phase by Lovastatin (Keyomarsi et al., *Cancer Res.* 50:3602-3609 (1991)). 76N cells were synchronized by growth factor deprivation and with Lovastatin, which gave very similar patterns of cyclin expression. Synchrony of both cell types was monitored by [3H]-thymidine incorporation.

Northern blot analysis revealed similarities and differences in the expression patterns of cyclins in these synchronized populations. Importantly, the patterns and timing of expression of G1 cyclins were very similar in both cell types. Cyclins D1, D3, C, and E mRNA levels were low to undetectable at the early hours in G1, peaked at mid (cyclin D1, D3 and C) to late G1 (cyclin E) and most of them dropped rapidly as cells entered S phase. Hence, the predominant accumulation of these cyclins in the G1 phase normal and tumor cells, suggests that aberration in G1 cyclins is not responsible for deranged growth of the ZR75T cells.

However, the overexpressed mRNAs for cyclins A and B and CDC2 in tumor cells show perturbed appearance, in the G1 phase of the cell cycle. In normal cells these mRNA levels were very tightly regulated, demonstrated by their dramatic fluctuations during the cell cycle, peaking by approximately 50 fold at S (15–21 h after release) for cyclin A and cdc2, and late S/G2 (21–24 h after release) for cyclin B. Subsequently, all rapidly disappeared at G2/M. On the other hand, in tumor cells, the basal levels of cyclin A and B mRNAs were high during the G1 phase and the maximal levels reached were over 10 fold higher than in the normal cells. In addition cyclin mRNA levels did not disappear as rapidly in G2/M in tumor cells as in normal cells, resulting in their prolonged overexpression, and possibly in higher protein levels.

These differences in the tumor cells of cyclin mRNA levels and patterns of expression during the cell cycle result in a deranged order of appearance. In normal 76N cells the order of expression of cyclins was: DI(C)-D3-E-A-B, as expected [Lu, X. P. et al., *J. Biol. Chem.* 267: 2841–2844 (1992) ]. In tumor cells, on the other hand, the mitotic cyclins appeared earlier than the G1 cyclins: B-A-D3(C)D1-E. This untimely appearance in the cell cycle is due to their high basal levels in G1 phase.

E. Mechanism of Cyclin mRNA Overexpression in Tumor Cells

The mechanism by which cyclins are deregulated in ZR75T appears to depend mainly upon greater stability of cyclin mRNAs in tumor cells. There were no gross genetic alterations of any cyclins in this tumor line compared to the normal cell DNA. To determine mRNA stabilities, the transcriptional inhibitor 5,6-dichlorobenzimidazole (DRB), which inhibits polymerase II activity responsible for mRNA synthesis, was used. DRB was used at 100µM, which in normal cells is sufficient to completely inhibit of c-myc mRNA transcription within less than 0.5 h after treatment. (c-Myc levels were undetectable in ZR75 cells). At several times after the addition of DRB, total RNA was extracted and subjected to Northern blot analysis. In all cases, cyclin and CDKmRNAs were more stable in tumor than in normal cells. The relative mRNA half-life values of cyclins and CDKs ranged from only 0.5 to 1.5 h in normal cells, whereas those in tumor cells ranged from 3 to 8 hours. The increase in stability of cyclin A, cyclin B and CDC2 mRNAs measured in tumor vs. normal cells quantitatively accounts for the higher mRNA steady state levels observed previously for this tumor line.

mRNAs of G1 cyclins were also significantly more stable in the ZR75T cells. This is surprising since G1 cyclins were not overexpressed in this cell line. Furthermore, mRNA of another gene, histone H4, was also more stable in tumor cells than in normal cells. Hence, the mechanism by which cyclin mRNAs are stabilized in this cell line does not depend on genetic alterations of cyclin genes.

F. Correlation of Cyclin E Protein Aberration to Different Stages of Breast Cancer For normal breast cells to become an invasive breast carcinoma, it progresses through the following stages: Normal—Hyperplasia—Atypical hyperplasia—Carcinoma in situ—Invasive breast cancer.

Figure 3:
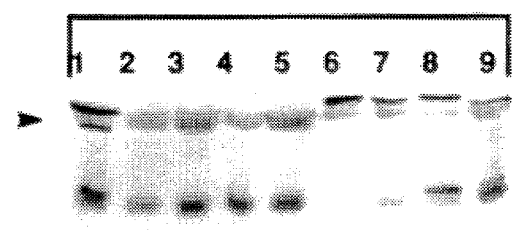
Figure 2:
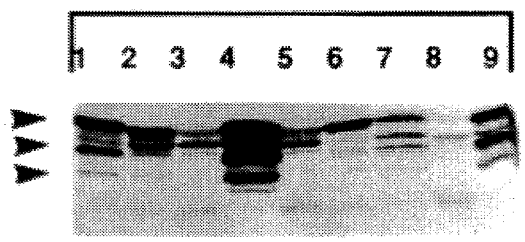
Figure 4:
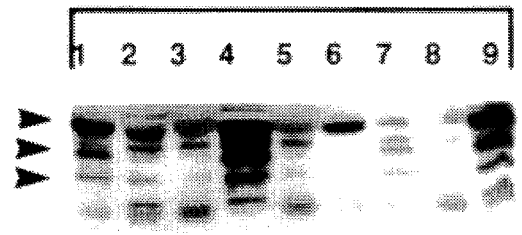

As described in Example 6, nine matched human malignant and normal mammary tissue samples were obtained from various types of breast cancer patients. Western blots performed on the samples revealed aberrant expression of cyclin E proteins in all nine samples (see FIGS. 1–4). Most of the tumor tissue samples were obtained from end stage breast cancer patients. Those from earlier stages showed cyclin E protein patterns similar to patterns from normal adjacent tissue; those from end stages showed several bands with increasing intensity, resembling the pattern obtained from the MDA-MB-157 tumor cell line. As breast cancer progresses to a more invasive form of the disease, it is reasonable to assume that the banding pattern for cyclin E is very intense, revealing several bands of differing molecular weights. Therefore, analysis of cyclin E expression can be used for staging of breast cancer.

G. Implications of Deranged Cyclin Expression Is cyclin E an oncogene?

Two lines of evidence suggest that cyclin E may be the prime candidate for oncogene action. First, the kinetics of appearance of cyclin E in late G1 phase (see Example 4; (Dulic et al., *Science* 257:1958–1961 (1992); Koff et al., *Science* 257:1689–1694 (1992); Lew et al., *Cell* 66:1197–1206 (1991)) coincides with timing of the restriction point protein that is required for moving cells toward S phase (Pardee, A.B., *Science* 246:603–608 (1989)). The deregulation of this process can lead to abnormal proliferation. Secondly, the deranged production of cyclin E protein in all cancer cell lines examined suggests an oncogenic role for cyclin E. Irrespective of their tumorigenicity potentials or estrogen receptor status, overexpression of one, two, or all three of the cyclin E-like proteins ranging in size from 35 to 50 kDa was observed, while in the normal cell strains (70N, 76N, and 81N) only one major protein of approximately 50 kDa was observed. Although the mechanisms responsible for deranged appearance of cyclin E (-like) protein(s) remain to be elucidated, the fact that only cyclin E protein is altered in all tumor lines suggests that the deregulation of this protein may be involved in transformation, and also that it can be used as a diagnostic tool for breast cancer.

Can overexpressed G2 cyclins function redundantly in G1?

Redundancy of cyclins has been observed in yeast (Richardson et al., *Cell* 59:1127–1133 (1988)) and Xenopus oocyctes (Swenson et al., *Cell* 47:861–870 (1986); Murray, A. W. and M. W. Kirschher, *Nature* 339:275–280 (1989)). Remarkably, G2 cyclins were generally overexpressed not only in most tumor lines but also in tumor tissue samples. Consequently, high levels of G2 cyclins appeared prior to G1 cyclins (in a tumor line that overexpresses G2 but not G1 cyclins) (see Example 5). The regulatory mechanisms which are deranged leading to abnormal proliferation of cells are thought to function in G1 phase (Pardee, A.B., *Science* 246:603–608 (1989)). Thus, the G2 cyclins in tumor cells may act redundantly and lose specificity as a result of their altered kinetic appearance in G1, and the coverexpression of CDC2. Thereby, the active kinase can function at a checkpoint different than its normal G2 target (Leopold et al., *Cell* 66:1207–1216 (1991)). It is suggested that cyclins function redundantly in cancer. Redundant excess cyclin can form a complex with the overexpressed CDK, whose elevated levels would trigger passage through all checkpoints of the cell cycle, resulting in decontrolled cell division and transformation.

Why are cyclins more stable in tumor cells?

An initial posttranscriptional derangement, such as increased RNA stability of cyclins, may lead to a cascade of changes resulting in increased net cyclin protein production. This preliminary step in the early stages of transformation may be compensated so as to keep the mRNA levels of G1 cyclins from rising. For example, cyclins D1, D3 and E mRNAs are more stable in ZR75T tumor cells than in 76N normal cells, though at the RNA level they are not overexpressed (see Examples 3 and 6). Upon loss of this feedback control, cyclin levels rise, as seen with overexpression of cyclins A, B and CDC2 RNAs and proteins in 90% of tumors examined (see Example 3); the general stability of cyclin mRNAs may lead to their increased abundances which could persist during all phases of the cell cycle (see Example 6). Cell cycle regulation of the overexpressed cyclins is also perturbed, as seen in the untimely appearances of cyclins A and B at the G1 phase of the cell cycle (see Example 5).

Observations that cyclins E and/or A may be intimately involved in the process of tumor formation are consistent with recent evidence on the ability of these cyclins to overcome a G1 block. Hinds et al. (*Cell* 70:993–1006 (1992)) report that a human osteogenic sarcoma cell line that lacks full length nuclear retinoblastoma protein (pRb) product but has received a wild-type pRb-encoding expression construct, arrests in G0 or G1 phase in a metabolically active state. Cotransfection of cyclin A or E overrides this pRb-induced block, causing cell cycle progression such that 60–70% of the pRb-positive cells were found in the S, G2, and M phases of the cell cycle. Hence, cyclin A and/or E is able to direct the cell into S phase. Similarly, it is proposed when these cyclins are overexpressed, as in the breast cancer cell lines, the cells will overcome checkpoint controls in the cell cycle.

The invention is further illustrated by the following Examples, which are not intended to be limiting in any way.

EXAMPLE 1 Materials and Methods

Materials

[Methyl-3H]thymidine (81 Ci/mmol; 81 Ci=37 GBq) and [a-$^{32}$P] dCTP (3000 Ci/mmol) were purchased from New England Nuclear, Boston, Mass. Lovastatin was provided by A. W. Alberts (Merck, Sharp and Dohme Research Pharmaceuticals, Rahway, N.J.). Mevalonic acid lactone and serum were purchased from Sigma Chemical Co. (St. Louis, Mo.) and cell culture medium from GIBCO Laboratories (Grand Island, N.Y.).

Cells and Culture Conditions

Normal human mammary epithelial cell strains 70N, 81N, and 76N were obtained from reduction mammoplasties of three individuals (Band, V. and Sager, R., *Proc. Natl. Acad. Sci. USA* 86:1249–1253 (1989)). The ZR75T cell line was derived from a human tumor produced in a nude mouse from a precloned derivative of ZR75-1-2, ZR-75-1; MDA-MB-157, MDA-MB-231, MDA-MB-436, T47D, BT-20, HBL-100, Hs578T, and SKBR3 cells were all obtained from the American Type Culture Collection. MCF-7 cells were obtained from Michigan Cancer Foundation. All cells were cultured in DFCI-1 medium as described (Band, V. and Sager, R., *Proc. Natl. Acad. Sci. USA* 86:1249–1253 (1989)) and were maintained free of Mycoplasma as determined by the MycoTect test kit (GIBCO).

Cell Synchronization

Synchronization by Lovastatin treatment or growth factor deprivation were performed as described [18]. Briefly, medium was removed 36–48 hours after the initial plating of ZR75T cells and replaced with fresh medium plus 20 μM Lovastatin for 33 hours. At time 0 hour, cells were stimulated with fresh medium containing 2 mM mevalonic acid. Cells were harvested at indicated times, and DNA synthesis and cell density were measured.

Synchronization of normal mammary epithelial 76N cells by growth factor deprivation is as follows: at 48 h following plating subconfluent 76N cells, and cells were washed three times and incubated in DFCI-3 medium for 48 h. DFCI-3 medium is DFCI-1 medium without essential growth factors (Band, V. and Sager, R., *Proc. Natl. Acad. Sci. USA* 86:1249–1253 (1989)). At time 0 h, cells were stimulated by the addition of DFCI-1 medium, and harvested at the indicated times thereafter.

Southern and Northern Blot Analysis

DNA isolation and Southern blot analysis were performed as described (Zajchowski et al., *Cancer Res.* 48:7041–7047 (1988)). Total RNA was isolated from frozen tissue samples, obtained from the National Disease Research Interchange, Eastern Division, by placing the tissue in 3 ml of guanidinium isothiocyanate and homogenizing with 10–20 strokes using a glass tube and Teflon pestle. Homogenates of tissues and cell lines were subjected to Northern blot analysis as described (Keyomarsi et al., *Cancer Res.* 50:3602–3609 (1991)). The DNA probes were prepared by random-primed labeling (Feinberg, A. P. and B. A. Vogelstein, *Anal. Biochem.* 132:6–13 (1983)) (Boehringer Mannheim) by [$\alpha$-32P]dCTP to a specific activity of $1\times10^9$ dpm/µg of DNA.

Total Cell Extract Preparation and Western Blot Analysis

Cell lysates were prepared by addition of one volume of sonication buffer (50 mM Tris-HCl (pH 7.4), 0.25 M NaCl, 1 mM DTT) to a cell pellet, and sonicating at 4° C. by using the cuphorn mode for five 2-minute bursts. Homogenates were centrifuged at 100,000×g for 45 minutes at 4° C. Aliquots of the supernatants were subjected to Western blot analysis as described (DeCaprio et al., *Proc. Natl. Acad. Sci. USA* 89:1795–1798 (1992)). The following hybridization conditions were used for each antibody: affinity purified anti-p34$^{cdc}$2 kinase peptide antibody (GIBCO) was incubated for 3 hours at 1 µg/ml; monoclonal antibodies C160 to human cyclin A or GNS II to human cyclin B were incubated overnight at 4° C. at a dilution of 1:3; affinity-purified rabbit anti-human cyclin E serum (specific for cyclin E) as described (Dulic et al., *Science* 257:1958–1961 (1992); Lees et al., *Genes & Dev.* 6:1874–1885 (1992)) was incubated for 3 hours at a dilution of 1:2500 in blocking buffer (20mM Tris-HCL (pH 7.5), 150 mM NaCl, 5% (wt/vol) bovine serum albumin, 5% (wt/vol) dried milk, 0.05% Tween 20). The blots were then developed with the detection reagents as directed by the manufacturer (cyclin E: ECL-Amersham; cyclins A and B and p34$^{cdc2}$, Promega).

EXAMPLE 2 Overexpression of Cyclins in Primary Breast Cancer Tissues

Total RNA was extracted from two human normal adjacent breast (NAT) tissue samples, and three human breast cancer tissues, corresponding to infiltrating ductal carcinoma, metastatic breast carcinoma, and infiltrating ductal carcinoma, respectively and analyzed by Northern blots, using 20 µg RNA/lane. Blots were hybridized with the indicated probes or 36B4 (Laborda, J., *Nucl. Acids Res.* 19:3998 (1991)), used for equal loading.

EXAMPLE 3 Cyclins are Overexpressed in Human Tumor Breast Epithelial Cell Lines

Northern blot and Western blot analysis of expression of cyclins in normal vs. tumor breast epithelial cells was performed. RNA was analyzed by Northern blots, using 20µg RNA/lane. Western blot analysis was conducted for cyclin A, cyclin B, cyclin E and CDC2 (molecular weights: cyclin E, 50 kDa; cyclin A, 60 kDa; cyclin B, 62 kDa; CDC2, 34 kDa) using cell extracts obtained from cell lines identical to those in panel A. Two extra cyclin E-like proteins were observed in the tumor cells at 42 and 35 kDa. Molecular weight standards were used on each gel to estimate the position of each band.

EXAMPLE 4 Expression of Cyclins in Synchronized Normal 76N and Tumor ZR75T Breast Cells Normal cells were synchronized by growth factor deprivation and tumor cells by Lovastatin (20 µM for 33 hours). At intervals following growth factor stimulation (normal cells) or addition of 2 mM mevalonate (tumor cells), total RNA was extracted from cells and analyzed by Northern blots, using 20 µg RNA/lane. Blots were hybridized with probes for cyclins D1, D3, E, A, B, and C, CDK2, CDC2, c-myc, and Histone H4,or 36B4 (used for equal loading). DNA synthesis rates in 76N (open symbols) and ZR75T cells (closed symbols) were measured by [$^3$H]-Tdr incorporation.

EXAMPLE 5 Stability of Cyclin RNAs in Normal vs. Tumor Breast Cells Following DRB Treatment Exponentially growing 76N and ZR75T cells were treated with 100 µM of the adenosine analog 5,6-dichloro-1-β-ribofuranosyl benzimidazole (DRB). At intervals following addition of DRB, RNA was extracted from cells and analyzed by Northern blots with the same probes as used in Example 5. Hybridization signals were normalized to the amount loaded, using signal intensity of 36B4 as loading control, and expressed as a percentage of the values at time 0 hour.

EXAMPLE 6 Analysis of Cyclin Expression in Breast Tissue Samples

Nine matched human malignant and normal mammary tissue samples were obtained from various types of breast cancer patients by surgical removal or autopsy and fresh frozen in liquid nitrogen within one hour following excision. Malignancy had been assessed by standard histopathological methods. Normal tissue was obtained from normal adjacent tissue (NAT) from the same patient as the malignant tissue sample.

Approximately 2 to 5 g of each matched tissue sample was analyzed. Cell lysates and western blots were performed as described above; the first blot using a polyclonal anti-sera to cyclin E, and the second using a monoclonal antibody to cyclin E, HE12, as described by Lees et al. (*Genes and Development* 6:1874–1885 (1992)).

As shown in FIGS. 1–4, aberrant cyclin E expression patterns are evident in breast cancer tissue compared with normal adjacent tissues. The breast cancer tissues displayed expression of other cyclin E proteins in addition to the normal 50 kDa protein.

EQUIVALENTS

Those skilled in the art will recognize, or be able to ascertain using no more than routine experimentation, many equivalents to specific embodiments of the invention described specifically herein. Such equivalents are intended to be encompassed in the scope of the following claims.

The invention claimed is:

1. A method of screening for the presence of carcinoma in a tissue sample from a human individual, comprising the steps of:
   a) obtaining a tissue sample from an individual suspected of having cancer, thereby obtaining a test sample;
   b) assessing the expression of cyclin E in the cells of the test sample; and
   c) comparing the cyclin E expression of the test sample with the cyclin E expression of a control sample,
   wherein the presence of aberrant expression of cyclin E in the test sample as compared with expression in the control sample is indicative of the presence of carcinoma.

2. The method of claim 1, wherein the expression of cyclin E in step (b) is assessed through western blotting in which a monoclonal antibody to cyclin E is used.

3. The method of claim 2, wherein the monoclonal antibody is HE12.

4. The method of claim 1, wherein the tissue sample is a breast tissue sample.

5. The method of claim 1, wherein the expression of cyclin E in step (b) is assessed through western blotting in which a polyclonal antisera to cyclin E is used.

6. The method of claim 1, wherein the aberrant expression of cyclin E in the test sample is overexpression of cyclin E.

7. The method of claim 6, wherein the aberrant expression of cyclin E in the test sample is over expression of a cyclin E protein of approximate molecular weight selected from the group consisting of 50 kDa, 42 kDa and 35 kDa, alone or in combination.

8. The method of claim 1, wherein the control sample in (c) is normal tissue from the individual from whom the test sample is obtained.

9. The method of claim 1, wherein the control sample in (c) is normal tissue from another individual.

10. A method of screening for the presence of carcinoma in a human individual, comprising the steps of:
    a) obtaining a tissue sample from an individual suspected of having cancer, thereby obtaining a test sample;
    b) assessing the expression of cyclin E mRNA in the cells of the test sample; and
    c) comparing the cyclin E mRNA expression of the test sample with the cyclin E mRNA expression of a control sample,
    wherein the presence of aberrant expression of cyclin E mRNA in the test sample as compared with expression in the control sample is indicative of the presence of carcinoma.

11. The method of claim 10, wherein the expression of cyclin E mRNA in step (b) is assessed through northern blotting.

12. The method of claim 10, wherein the control sample in (c) is normal tissue from the individual from whom the test sample is obtained.

13. The method of claim 10, wherein the control sample in (c) is normal tissue from another individual.

14. A method of screening for the presence of human breast carcinoma in a breast tissue sample from an individual, comprising the steps of:
    a) obtaining a breast tissue sample from an individual suspected of having breast cancer, thereby obtaining a test sample;
    b) assessing the expression of cyclin E in the test sample; and
    c) comparing the expression of cyclin E in the test sample with the expression of cyclin E in a control sample,
    wherein the presence of aberrant expression of cyclin E in the test sample as compared with expression in the control sample is indicative of the presence of breast carcinoma.

15. The method of claim 14, wherein the aberrant expression of cyclin E in the test sample is overexpression of cyclin E.

16. The method of claim 14, wherein the aberrant expression of cyclin E in the test sample is overexpression of a cyclin E protein of approximate molecular weight selected from the group consisting of 50 kDa, 42 kDa and 35 kDa, alone or in combination.

17. The method of claim 14, wherein the control sample in (c) is normal breast tissue from the individual from whom the test sample is obtained.

18. The method of claim 14, wherein the control sample in (c) is normal tissue from another individual.

19. A method of screening for the presence of human breast carcinoma in a breast tissue sample from an individual, comprising the steps of:
    a) obtaining a breast tissue sample from an individual suspected of having breast cancer;
    b) preparing cell lysates of the tissue sample, thereby generating a cell lysate preparation;
    c) subjecting the cell lysate preparation to Western blotting using an anti-cyclin E agent, thereby generating a test blot; and
    d) comparing the results of the test blot with a western blot of a cell lysate preparation from a control sample,
    wherein the presence of aberrant expression of cyclin E in the test blot as compared with expression in the control blot is indicative of the presence of breast carcinoma.

20. The method of claim 19, wherein the anti-cyclin E agent in (c) is a polyclonal antisera to cyclin E.

21. The method of claim 19, wherein the anti-cyclin E agent in (c) is a monoclonal antibody to cyclin E.

22. The method of claim 21, wherein the anti-cyclin E antibody is HE12.

23. The method of claim 19, wherein the control sample in (d) is normal mammary epithelial cells from a reduction mammoplasty.

24. The method of claim 19, wherein the control sample in (d) is normal tissue from the patient.

25. The method of claim 19, wherein the test blot in (c) reveals overexpression of a cyclin E protein of approximate molecular weight selected from the group consisting of 50 kDa, 42 kDa, and 35 kDa, alone or in combination.

26. A method of detecting carcinoma cells in a sample of cells, comprising the steps of:
    a) obtaining a sample of cells to be assessed, the sample referred to as test cells;
    b) determining the level of cyclin E protein expression in the test cells; and
    c) comparing the level of cyclin E protein expression in the test cells with the level of cyclin E protein expression in normal cells of the same type as the test cells,
    wherein overexpression of cyclin E protein in test cells than in normal cells of the same type is indicative of carcinoma cells.

27. The method of claim 26, wherein the test cells are breast tissue cells.

28. The method of claim 26, wherein the level of cyclin E protein expression determined in (b) is the level of cyclin E protein selected from the group consisting of:
1) cyclin E protein of approximately 50 kDa molecular weight;
2) cyclin E protein of approximately 42 kDa molecular weight;
3) cyclin E protein of approximately 35 kDa molecular weight;
4) a combination of two cyclin E proteins of (1), (2) and (3) above; and
5) a combination of the three cyclin E proteins of (1), (2) and (3) above.

29. A method of screening for the presence of carcinoma in a tissue sample from a human individual, comprising the steps of:
a) obtaining a tissue sample from an individual suspected of having cancer, thereby obtaining a test sample;
b) assessing the copy number of the cyclin E genes in the cells of the test sample; and
c) comparing the copy number of the cyclin E genes in the test sample with the copy number of the cyclin E genes in a control sample,
wherein the presence of an amplified number of cyclin E genes in the test sample as compared with the control sample is indicative of the presence of carcinoma.

30. The method of claim 29, wherein the copy number of the cyclin E genes in step (b) is assessed through southern blotting.

31. A method of screening for the presence of human breast carcinoma in a breast tissue sample from an individual, comprising the steps of:
a) obtaining a breast tissue sample from an individual suspected of having breast cancer, thereby obtaining a test sample;
b) assessing the copy number of the cyclin E gene in the cells of the test sample; and
c) comparing the copy number of the cyclin E gene in the test sample with the copy number of the cyclin E gene on a control sample,
wherein the presence of an amplified number of cyclin E genes in the test sample as compared with the control sample is indicative of the presence of breast carcinoma.

32. The method of claim 31, wherein the copy number of the cyclin E gene in step (b) is assessed through southern blotting.

33. A method of screening for the presence of human breast carcinoma in an individual, comprising the steps of:
a) obtaining a blood sample from an individual suspected of having breast cancer, thereby obtaining a test sample;
b) assessing the cyclin E protein in the test sample; and
c) comparing the cyclin E protein in the test sample with the cyclin E protein in a control sample,
wherein the presence of aberrant cyclin E in the test sample as compared with the control sample is indicative of the presence of breast carcinoma.

34. The method of claim 33, wherein the aberrant cyclin E in the test sample is a cyclin E protein of approximate molecular weight of 42 kDa or 35 kDa, alone or in combination.

35. A method of determining the stage of progression of human breast carcinoma in a tissue sample from an individual, comprising the steps of:
a) obtaining a tissue sample from an individual suspected of having breast cancer;
b) preparing cell lysates of the tissue sample, thereby generating a cell lysate preparation;
c) subjecting the cell lysate preparation to Western blotting using an anti-cyclin E agent, thereby generating a test blot; and
d) comparing the results of the test blot with a western blot of a cell lysate preparation from a control sample,
wherein an increased degree of intensity of the aberrant expression of cyclin E in the test blot as compared with expression in the control blot corresponds with a later stage of breast cancer.

36. The method of claim 35, wherein the test blot in (c) reveals overexpression of a cyclin E protein of approximate molecular weight selected from the group consisting of 50 kDa, 42 kDa, and 35 kDa, alone or in combination.

37. A method of screening for the presence of human breast carcinoma in a breast tissue sample from an individual, comprising the steps of:
a) obtaining a breast tissue sample from an individual suspected of having breast cancer, thereby obtaining a test sample;
b) assessing the expression of cyclin E in the test sample; and
c) comparing the expression of cyclin E in the test sample with the expression of cyclin E in a control sample,
wherein the presence of aberrant expression of cyclin E in the test sample as compared with expression in the control sample is indicative of the presence of breast carcinoma.

38. A method of screening for the presence of carcinoma in a human individual, comprising the steps of:
a) obtaining a tissue sample from an individual suspected of having cancer, thereby obtaining a test sample;
b) assessing the expression of cyclin mRNA in the cells of the test sample; and
c) comparing the cyclin mRNA expression of the test sample with the cyclin mRNA expression of a control sample,
wherein the presence of untimely appearance of mitotic cyclin mRNA in the test sample as compared with expression in the control sample is indicative of the presence of carcinoma.

39. The method of claim 38, wherein the order of appearance of the cyclin mRNA is cyclin B-A-D3(C)D1-E.

* * * * *